United States Patent [19]

Ben-Bassat et al.

[11] Patent Number: 4,870,017

[45] Date of Patent: Sep. 26, 1989

[54] BACTERIAL METHIONINE N-TERMINAL PEPTIDASE

[75] Inventors: Arie Ben-Bassat, Concord; Keith A. Bauer, Oakland; Shing Chang, Oakland; Sheng-Yung Chang, Oakland, all of Calif.

[73] Assignee: Cetus Corporation, Emeryville, Calif.

[21] Appl. No.: 778,414

[22] Filed: Sep. 20, 1985

[51] Int. Cl.[4] ............... C12N 9/48; C12N 15/00
[52] U.S. Cl. .................... 435/212; 435/68; 435/172.3; 435/252.33; 435/317.1
[58] Field of Search ............ 260/112.5; 530/409, 530/339, 402; 935/11, 28, 69, 79; 435/70, 71, 91, 212, 255, 256, 317

[56] References Cited

U.S. PATENT DOCUMENTS 4,338,397  7/1982  Gilbert .................. 435/68
4,350,764  9/1982  Baxter .................. 435/69
4,465,773  8/1984  Dean et al. ............. 435/253
4,667,017  5/1987  Ishida .................. 530/402

FOREIGN PATENT DOCUMENTS 127305  4/1984  European Pat. Off. .

OTHER PUBLICATIONS

Bally et al., Fems Microbiology Letters (1983) pp. 261–265.
Alberts et al., Molecular Biology of the Cell (1983) p. 14.
Juluis et al., Cell, vol. 32 1983 pp. 839–852.
Bally et al., Mol. Gen. Genet. 1984 195 507–510.
Brown et al., BioChem. and Biophys. Res. Comm. 1971 42 (3)390–397.
Fasman, G. O., Ed., CRC Handbook of Biochem. & Mol. Biol., III:308–313.
Yoshida, A., et al., J. of Biol. Chem. (1972) 247:952–957.
Suda, H., et al., Biochim. et Biophys. Acta (1980) 616:60–67.
Freitas, J. O., Jr., et al., Int. J. Biochem. (1981) 13:991–997.
Miller, C. G., et al., J. of Bacteriol. (1978) 135:603–611.
Tsunasawa, S., et al., J. of Biol. Chem. (1985) 260:5382–5391.
Sherman, F., et al., BioEssays, 3:27–31.

Primary Examiner—Thomas G. Wiseman
Assistant Examiner—Patricia Carson
Attorney, Agent, or Firm—Kate H. Murashige; Albert P. Halluin

[57] ABSTRACT

Methods of obtaining N-terminal methionine-free proteins are described. The methods employ a novel enzyme, E. coli methionine aminopeptidase either in vitro or in vivo. For in vivo application, plasmid-borne DNA encoding the peptidase is transformed into a bacterial host which produces the desired protein.

11 Claims, 3 Drawing Sheets

```
              1                    5                   10
       Ala[1]-Ile-Ser-Ile-Lys-Thr-Pro-Glu-Asp-Ile-Glu-Lys-Met-Arg- 15                   20                  25
       -Val-Ala-Gly-Arg-Leu-Ala-Ala-Glu-Val-Leu-Glu-Met-Ile-Glu- 30                   35                  40
       -Pro-Tyr-Val-Lys-Pro-Gly-Val-[Ser-Thr][2]-Glu-Leu-Asp-Arg- 45                   50                  55
       -Ile-X[3]-Asn-Asp-Tyr-Ile-Val-Asn-Glu-Gln-His-Ala-Val-Ser- 60                   65
       -Ala-[Asn/Glu-Leu][4]-Gly-Tyr-His-Gly-Tyr-Pro-Lys-
```

[1] An equal amount of PTH-Met was observed in cycle 1, due to free methionine in the preparation.

[2] The products of cycles 36 and 37 were accidentally mixed during sample preparation. A quantitative analysis of the carryover into cycle 38 suggests that the order of amino acids is Ser-Thr rather than Thr-Ser.

[3] No identification could be made in cycle 43. However, a substantial amount of PTH-dehydroalanine was observed. This derivative is formed both from serine and from cysteine.

[4] A fraction collector problem in the sequencer caused two or more samples to be delivered.

FIG. I $$\overset{1}{\text{Ala}}{}^{1}\text{-Ile-Ser-Ile-Lys-Thr-Pro-Glu-Asp-Ile-Glu-Lys-Met-Arg-}$$
(positions 1, 5, 10)

$$\text{-Val-Ala-Gly-Arg-Leu-Ala-Ala-Glu-Val-Leu-Glu-Met-Ile-Glu-}$$
(positions 15, 20, 25)

$$\text{-Pro-Tyr-Val-Lys-Pro-Gly-Val-[Ser-Thr]}^{2}\text{-Glu-Leu-Asp-Arg-}$$
(positions 30, 35, 40)

$$\text{-Ile-X}^{3}\text{-Asn-Asp-Tyr-Ile-Val-Asn-Glu-Gln-His-Ala-Val-Ser-}$$
(positions 45, 50, 55)

$$\text{-Ala-[Asn/Glu-Leu]}^{4}\text{-Gly-Tyr-His-Gly-Tyr-Pro-Lys.}$$
(positions 60, 65)

1     An equal amount of PTU-Met was observed in cycle 1, due to free methionine in the preparation.

2     The products of cycles 36 and 37 were accidentally mixed during sample preparation. A quantitative analysis of the carryover into cycle 38 suggests that the order of amino acids is Ser-Thr rather than Thr-Ser.

3     No identification could be made in cycle 43. However, a substantial amount of PTM-dehydroalanine was observed. This derivative is formed both from serine and from cysteine.

4     A fraction collector problem in the sequencer caused two or more samples to be delivered.

FIG. 2

```
   1 GATCGGAAGTCCGGCGCGCTTTATACCACAAATACGTCGTGGACACCAATAATTGTTGGCGC
                     (BssHII)

63 TGTGTACAGCATCAGACGTCGAATTTTCTATTATAGAAAACCTTCAGTGGCACGTTTGGC

P1 *=====>
 123 GAAATTCAGAATGATTCTCAATTTGCCCGGGTGTGATACCATTGACGGCACTTACATATA
            ------       (SmaI)                              ------

P2*------>
 183 TATTGTCGGTATCACCGACGCTGATGGACAGAATTAATGGCTATCTCAATCAAGACCCCA
        <<<<<<***>>>>>>                  MetAlaIleSerIleLysThrPro      8

243 GAAGATATCGAAAAAATGCGCGTCGCTGGCCGACTGGCTGCCGAAGTGCTGGAGATGATC
     GluAspIleGluLysMetArgValAlaGlyArgLeuAlaAlaGluValLeuGluMetIle    28

303 GAACCGTATGTTAAACCGGGCGTCAGCACCGGCGAGCTGGATCGCATCTGTAATGATTAC
     GluProTyrValLysProGlyValSerThrGlyGluLeuAspArgIleCysAsnAspTyr    48

363 ATTGTTAATGAACAACACGCGGTTTCTGCCTGCCTCGGCTATCACGGCTATCCGAAATCC
     IleValAsnGluGlnHisAlaValSerAlaCysLeuGlyTyrHisGlyTyrProLysSer    68

423 GTTTGCATCTCTATTAATGAAGTGGTGTGCCACGGTATCCCGGACGATGCTAAGCTGCTG
     ValCysIleSerIleAsnGluValValCysHisGlyIleProAspAspAlaLysLeuLeu    88

483 AAAGATGGCGATATCGTTAACATTGATGTCACCGTAATCAAAGATGGTTTCCACGGCGAT
     LysAspGlyAspIleValAsnIleAspValThrValIleLysAspGlyPheHisGlyAsp   108

543 ACCTCGAAAATGTTTATCGTCGGTAAGCCGACCATCATGGGCGAACGTCTGTGCCGCATC
     ThrSerLysMetPheIleValGlyLysProThrIleMetGlyGluArgLeuCysArgIle   128

603 ACGCAAGAAAGCCTGTACCTGGCGCTACGCATGGTAAAACCAGGCATTAATCTGCGCGAA
     ThrGlnGluSerLeuTyrLeuAlaLeuArgMetValLysProGlyIleAsnLeuArgGlu   148

663 ATCGGTGCGGCGATTCAGAAATTTGTCGAAGCAGAAGGCTTCTCCGTCGTTCGTGAATAT
     IleGlyAlaAlaIleGlnLysPheValGluAlaGluGlyPheSerValValArgGluTyr   168

723 TGCGGACACGGTATTGGTCGCGGCTTCCATGAAGAACCGCAGGTGCTGCACTATGACTCC
     CysGlyHisGlyIleGlyArgGlyPheHisGluGluProGlnValLeuHisTyrAspSer   188

783 CGTGAAACCAACGTCGTACTGAAACCTGGGATGACGTTCACCATCGAGCCAATGGTCAAC
     ArgGluThrAsnValValLeuLysProGlyMetThrPheThrIleGluProMetValAsn   208

843 GCGGGTAAAAAAGAGATCCGCACCATGAAAGATGGCTGGACGGTAAAAACCAAAGATCGC
     AlaGlyLysLysGluIleArgThrMetLysAspGlyTrpThrValLysThrLysAspArg   228

903 AGCTTGTCTGCACAATATGAGCATACTATTGTGGTGACTGATAACGGCTGCGAAATTCTG
     SerLeuSerAlaGlnTyrGluHisThrIleValValThrAspAsnGlyCysGluIleLeu   248

963 ACGCTACGCAAGGATGACACCATCCCGGCGATAATCTCGCACGACGAATAAGATGAAG
     ThrLeuArgLysAspAspThrIleProAlaIleIleSerHisAspGlu...    <<<      264

1021 CCGGCGAATGCCGGCTTTTTTAATGCGATAATTTAATCTTATGGGTGGCGCACAATGAAT
     <<<<<<****>>>>>>>>

1081 ACCCTTCCAGAACAGTACGCAAACACCGCTCTCCCCACCCTGCCCGGTCAACCGCAAAAT

1141 CCATGCGTCTGGCCCCGTGATGAATTAACCGTCGGTGGGATAAAAGCCCATATCGAT
                                                   (ClaI) >
```

BACTERIAL METHIONINE N-TERMINAL PEPTIDASE

TECHNICAL FIELD

The invention relates to production of proteins, especially foreign proteins, lacking an N-terminal methionine, in bacterial systems using recombinant techniques. More specifically, it relates to a peptidase specific for N-terminal methionine which can be used in vitro or used to create a superior bacterial host containing elevated levels of peptidase for complete processing of mature proteins in these systems.

BACKGROUND ART

Production of foreign proteins in bacterial hosts is now well established. In relatively standard procedures, the gene sequence encoding the desired protein is placed under the control of regulatory sequences indigenous to or compatible with the host and transformed into the host bacterium. In general, there are three major ways in which this can be accomplished: (1) the DNA encoding the desired protein can be fused in reading frame with a bacterial gene already under the control of the bacterial regulatory sequences to obtain a "fusion protein"; (2) the desired coding sequences can be fused in reading frame with an operable leader sequence resulting in a secreted protein; or (3) the desired coding sequence is placed immediately downstream from an ATG start codon which results in "direct" expression to obtain the "mature" protein. In this last instance, the mature protein is not secreted but is found in an intracellular location, often as a refractile or inclusion body.

It is often left unstated, but well recognized by practitioners in the art, that the mature protein formed by the direct expression of ATG-preceded coding sequences frequently bears an N-terminal methionine which is the translation product of the ATG. Depending on the particular recombinant protein, and on the circumstances of its production, more or less of it may be processed in the cell to remove this N-terminal Met residue, but, in general, at least some, and usually a substantial portion of the recombinant protein produced does bear this unwanted foreign residue. Its presence is not completely harmless. When the resulting proteins are used therapeutically, what would ordinarily be an autologous protein to the recipient (for example, human growth hormone (hGH) as administered to humans) now contains a peptide sequence which is unfamiliar to the recipient. The result is predicatable. An immune response may be mounted to the unfamiliar sequence and a therapeutically important peptide now becomes an immunogen.

In addition to foreign proteins, mature native proteins and bacterial proteins from other genera or species are also often incompletely processed. Examples of this phenomenon include *E. coli* aspartate transcarbamylase (R-chain), *E. coli* tryptophan synthestase A protein, and *E. coli* bacteriophage T4 lysozyme. (Fasman, G. O., Ed., *CRC Handbook of Biochemistry & Molecular Biology*, III:308–313.)

Others have attempted to resolve the N-terminal methionine problem and to produce N-terminal "Metless" peptides or proteins in various ways. Baxter (U.S. Pat. No. 4,350,764) uses in vitro treatment with the protease trypsin to cleave a precursor protein after protecting alternate cleavage sites. Fusion proteins have also been synthesized where the desired coding sequence is preceded by ATG, thus providing an "internal" methionine in the fusion cleavable by CNBr. Not only does this involve an extra preparation step, but has the more serious defect that the protein or peptide is also cleaved at any methionine residues in the remaining sequence. EPO publication 127,305, published 5 December 1984, to Genentech discloses the production of Met-less hGH by employing a coding sequence which includes the native hGH leader peptide which apparently is workable in certain bacterial hosts to effect secretion of the resulting hGH. Gilbert (U.S. Pat. No. 4,338,397) has employed the penicillinase leader sequence to effect the secretion of presumably N-terminal Met-less β-globin. U.S. Ser. No. 715,653, filed 25 March 1985, assigned to the same assignee and incorporated herein by reference, discloses the use of the leader sequence for bacterial phospholipase A (phoA) to effect secretion of certain, but not all, recombinant peptides.

None of the foregoing approaches provides a universal solution to the problem. Faced with the necessity to produce any particular recombinant protein in N-terminal Met-less form, the practitioner needs to select from a repertoire of possibilities a procedure suitable for the particular peptide to be produced. The method of the invention described below expands this repertoire to provide still another pattern of applicability.

DISCLOSURE OF THE INVENTION

The invention furnishes a convenient enzyme for assuring the processing of N-terminal methionine residues from bacterially produced recombinant or other proteins. Also provided is the DNA encoding this enzyme permitting genetic manipulation of the recombinant host organism to effect the desired processing in vivo without the necessity of the separate step. The availability of the peptidase enzyme of the invention thus permits production in bacterial hosts of recombinant proteins which have reduced immunogenicity when used therapeutically.

In one aspect, the invention relates to a peptidase which cleaves N-terminal methonine residues from certain protein sequences—i.e., a methionine amino peptidase or N-terminal exopeptidase. The enzyme will be referred to herein as Met-aminopeptidase. In other aspects, the invention relates to a recombinant DNA sequence encoding the Met-aminopeptidase, to plasmids bearing this sequence, and to microbial hosts transformed with these plamids, as well as to methods for producing N-terminal Met-less recombinant proteins in bacterial hosts or in vitro using the materials of the invention. In still another aspect, the invention relates to a method to obtain a bacterial strain with high Met-aminopeptidase activity comprising screening generally peptidase-deficient (but not Met-aminopeptidase deficient) transformant hosts wherein the transformant has had introduced a portion of its own genome.

BRIEF DESCRIPTION OF THE DRAWINGS

FIG. 1 shows the N-terminal amino acid sequence determined from the protein of the Met-aminopeptidase of the invention.

FIG. 2 shows DNA sequence encoding the Met-aminopeptidase illustrated in FIG. 1.

MODES OF CARRYING OUT THE INVENTION

A. Definitions

Figure 3:
FIG. 3 shows an SDS gel of purified recombinant IL-2 before and after processing with the enzyme of the invention.

As used herein, "Met-aminopeptidase" refers to an enzyme which specifically cleaves the N-terminal methionine residue from a peptide sequence, and does not cleave at internal methionine residues or at N-terminal residues other than methionine. The Met-aminopeptidase of the invention appears to be specific for particular peptide sequences depending on the residue occupying position 2 and on the secondary or tertiary structure of the substrate protein or peptide. The precise specificity of the enzyme in this regard cannot be determined without testing nearly an infinite number of substrates; however, a useful rule of thumb is set forth by Sherman, F., et al, *Bio Essays* (1985) 3:27-31. Sherman et al based their considerations for specificity of Met-aminopeptidases on the observed forms of mutants of iso-1-cytochrome-C from yeast, and on theoretical considerations derived from these observations. They conclude that methionine is usually cleaved from residues with a side chain having a radius of gyration of 1.29 Å or less, but not cleaved from residues with larger side chains. This is consistent with the observation that mutationally altered iso-1-cytochrome-C taken in consideration with other published sequences of other proteins from procaryotic and eucaryotic systems indicate that N-terminal methionine is cleaved when it precedes residues of alanine, cysteine, glycine, proline, serine, threonine, or valine, but not when it precedes residues of arginine, asparagine, aspartic acid, glutamine, glutamic acid, isoleucine, leucine, lysine, or methionine. These results are consistent with those set forth in the illustrations below. However, this specificity is intended as a general guideline, and it should be borne in mind that even the precise specificity of the aminopeptidase used to illustrate the present invention is not determined with precision. Therefore, in order to fall within the definition of "Met-aminopeptidase", the enzyme needs only to meet the requirement of specific cleavage of N-terminal methionine without cleavage of internal methionine residues and without cleavage at other N-terminal residues.

The preferred Met-aminopeptidases of the invention have N-terminal amino acid sequences substantially equivalent to that shown in FIG. 1, and total amino acid sequences substantially equivalent to that encoded by the DNA illustrated in FIG. 2. By "substantially equivalent" is mean that the protein retains the same activity in specifically cleaving N-terminal methionine residues from particular peptide or protein sequences with fundamentally the same underlying specificity with respect to secondary and tertiary structures or subsequent amino acid residues, even though minor alterations in amino acid sequence may be present. Such alteration, interchange, addition, or deletion of one or several amino acids in the sequence which do not appreciably alter activity do not remove a particular protein from this definition.

Of course, included as well are the neutral and salt forms of the Met-aminopeptidases, as well as forms which contain additional non-protein moieties such as glycosylation, lipid residues, or acetylation.

"Peptidase-deficient" strain refers to a bacterial strain which is lacking in at least four peptidases other than Met-aminopeptidase which peptidases are normally found in the wild type.

"N-terminal Met-less" protein, as used in this application, specifically refers to a protein lacking an N-terminal methionine, but which might include methionine residues elsewhere in its primary structure. The coding sequence for the protein will have an immediately preceding ATG start codon in reading frame. "N-terminal Met-less" is used as a convenient shorthand term so that the conditions surrounding this state need not be repetitively given. Specifically, "N-terminal Met-less" does not mean, in the context of this invention, that there are necessarily no methionine residues whatsoever in the protein sequence, nor is it intended to include proteins which had no possibility of an N-terminal methionine in the first place, such as those produced as fusion proteins or as secreted proteins, preceded before processing by a signal sequence. Thus, as used herein, "N-terminal Met-less protein" refers to a protein which is encoded by a DNA sequence wherein the mature protein is immediately preceded by an in-reading-frame ATG start condon and not part of a fusion to be subsequently cleaved by CNBr or other reagents. In the case of recombinant proteins, the constructions are clearly specified; for native or naturally recombined DNA sequences, the constructions may not be as easily defined.

"Cells", "cell cultures", "host cells", and the like refer to subject cells for recombinant DNA manipulations. As would be apparent from the context, these cells may be candidates for, or resultants of, transfer of new DNA sequences according to recombinant techniques. Techniques which are suitable for DNA uptake by cells include most prominently, in vitro transformation. However other techniques such as transduction or conjugation may also be used. The definition further includes the progeny of the cells directly referred to. It is understood that such progeny may not be precisely identical in DNA content to their parents, but such progeny are included in the definition so long as alterations due, for example, to accidental or deliberate mutation do not destroy the ability of the cells to exhibit the properties conferred by the introduced DNA in a manner similar to that exhibited by their parents.

B. General Description

The present invention achieves the production of N-terminal Met-less recombinant proteins in bacterial hosts through the use of a Met-aminopeptidase. In the most preferred embodiment, the Met-aminopeptidase is generated at high levels in situ and processes the recombinant or other protein in vivo in the bacterial host. However, it is also possible to isolate or extract the desired recombinant or other protein from the host cells and treat the extract in vitro with the Met-aminopeptidase obtained independently from a bacterial source.

With respect to the Met-aminopeptidase per se, this enzyme has been produced and the DNA encoding it recovered by taking advantage of the ease in screening *E. coli* strains which are generally peptidase deficient for enhanced production of the Met-aminopeptidase encoded in their own genome. In this process, a source of plasmid-borne and amplified DNA encoding Met-aminopeptidase is obtained, and the enzyme can then be prepared and purified directly from these cells. In addition co-transformation of recombinant hosts with this plasmid DNA, along with the expression vector for a desired recombinant protein, results in in situ production of the recombinant protein in N-terminal Met-less form.

A number of *E. coli* strains which are deficient in a multiplicity of peptidases ordinarily found in wild-type bacteria are known. For example, Miller, C. G., et al, *J. Bacteriol* (1978) 135:603-611, discloses a number of bacterial strains which are peptidase deficient. One of these strains, CM89, which is deficient in peptidase N, peptidase A, peptidase B, peptidase D, and peptidase Q, was used in the illustration below. However, other peptidase-deficient mutants of bacterial strains could be used as well.

Presumably, the genome in these strains still contains the sequence encoding the Met-aminopeptidase activity, and the genomic DNA is therefore used to construct a library by digestion with an appropriate restriction enzyme and cloning the fragments into carrier vectors. A variety of such carrier vectors is available, including the pUC series and pBR322. Plasmid DNA may then, if desired, be amplified using any convenient wild-type host before isolation of the plasmid DNA and transformation, back into the peptidase-deficient strain for screening.

The transformed peptidase-deficient bacteria are then screened for production of the desired Met-aminopeptidase for assaying crude extracts for their ability to cleave an appropriate substrate. A strain which shows an elevated level of Met-aminopeptidase is then conveniently used as a source for this enzyme or as a source of plasmid DNA for co-transformation with the expression vector for a recombinant protein.

Large numbers of recombinant proteins are candidates for production as mature proteins in processed form, free of N-terminal methionine, using the method of the invention. For example, lymphokines such as IL-2, IL-1; the $\alpha$- and $\gamma$-interferons ($\beta$-interferon normally contains an N-terminal methionine in its mature form); tumor necrosis factor; and other proteins associated with the lymphatic systems are thus produced. Also, various hormones, such as growth hormones, insulin, ACTH, endorphins, and other peptide hormones can be produced recombinantly. Other candidates for recombinant production include enzymes such as tissue plasminogen activator, urokinase, and enzymes useful in industrial applications such as alcohol dehydrogenase. The foregoing are merely exemplary, and, in principle, any desired protein, once its gene is obtained, can be expressed as a mature protein by linking it in reading frame to an immediately upstream ATG start codon and providing the necessary control sequences. The method of the invention permits any of these proteins to be conveniently produced without N-terminal methionine.

As stated above, the Met-aminopeptidase may be used in two general ways. The enzyme may be isolated from the specific cells producing it in relatively large quantity from plasmid-borne DNA, and added to an in vitro reaction mixture to effect N-terminal methionine processing, or the Met-aminopeptidase encoding plasmids may be cotransformed along with expression vectors for a desired protein into a recombinant bacterial host to permit in vivo processing. In the in vitro approach, the purified Met-aminopeptidase is added to a reaction mixture containing unprocessed protein and suitable salt and buffer. The reaction mixture is incubated at a temperature of preferably about 30° C. overnight to permit the processing to occur. The enzyme exhibits a requirement for cobalt ion and for phosphate. A typical reaction mixture might contain about 1 mg/ml substrate protein, about 80 $\mu$g/ml of enzyme in pH 7-8 phosphate buffer and about 0.2 mM cobalt ion. The foregoing typical mixture is, of course, merely illustrative and the concentrations of the components can be varied in a continuum depending on the nature of the substrate and the time and temperature conditions employed. Complete processing can be verified by measuring the amount of methionine residue released, by comparing the mobility on SDS PAGE of the processed and unprocessed subject protein, or by sequencing the substrate material contained in the mixture.

In the in vivo approach, plasmid DNA is isolated from the Met-aminopeptidase source strain and used to transform cells which already harbor or which are concomitantly or subsequently transformed to harbor an expression system for the proteins. When used in bacterial sources for bacterial enzymes, the unprocessed substrates may be produced as a part of the complement of proteins ordinarily generated by the microorganism. More commonly, the peptidase generated in situ is used to process recombinantly produced proteins and the cells must be at some point transformed to contain the expression system for the desired protein.

C. Standard Techniques

Standard methods for transformation of bacteria, selection of successful transformants using markers, preparation of plasmid vectors, and screening of gene or cDNA banks are now well understood in the art. For convenience, a selection of procedures particularly useful in the example set forth below are presented here. Most such methods, or alternative workable ones, are found in Maniatis, et al, *Molecular Cloning—A Laboratory Manual* (1982), Cold Spring Harbor Press.

C.1. Hosts and Control Sequences

The cells suitable for cotransformation with vectors bearing Met-aminopeptidase and expression systems for protein are bacterial. Most frequently the hosts are various strains of *E. coli*. However, other microbial strains may also be used, such as bacilli, for example *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar, et al, *Gene* (1977) 2:95. pBR322 contains genes for ampicillin and tetracycline resistance, and thus provides additional markers which can be either retained or destroyed in constructing the desired vector. Commonly used procaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang, et al, *Nature* (1977) 198:1056) and the tryptophan (trp) promoter system (Goeddel, et al *Nucleic Acids Res* (1980) 8:4057) and the lambda derived $P_L$ promoter and N-gene ribosome binding site (Shimatake, et al, *Nature* (1981) 292:128), which has been made useful as a portable control cassette, as set forth in copending application Ser. No. 578,133, filed February 8, 1984, and assigned to the same assignee. However, any available promoter system compatible with procaryotes can be used.

C.2. Transformations

The cells are transformed using calcium treatment employing calcium chloride, as described by Cohen, S.

N., *Proc Natl Acad Sci (USA)* (1972) 69:2110, or the RbCl₂ method described in Maniatis, et al, (supra).

C.3. Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 $\mu$g of plasmid or DNA sequence is cleaved by one unit of enzyme in about 20 $\mu$l of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol followed by running over a Sephadex G-50 spin column. If desired, size separation of the cleaved fragments may be performed by polyacylamide gel or agarose gel electrophoresis using standard techniques. A general description of size separations is found in *Methods in Enzymology* (1980) 65:499-560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM MgCl₂, 6 mM DTT and 5-10 $\mu$M dNTPs. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex G-50 spin column. Treatment under appropriate conditions with S1 nuclease results in hydrolysis of any single-stranded portion.

Synthetic oligonucleotides are prepared by the triester method of Matteucci, et al (*J Am Chem Soc* (1981) 103:3185) or using commercially available automated oligonucleotide synthesizers. Kinasing of single strands prior to annealing or for labeling is achieved using an excess, e.g., approximately 10 units of polynucleotide kinase to 0.1 nmole substrate in the presence of 50 mM Tris, pH 7.6, 10 mM MgCl₂, 5 mM dithiothreitol, 1-2 mM ATP, 1.7 pmoles $\gamma$32P-ATP (2.9 mCi/mmole), 0.1 mM spermidine, 0.1 mM EDTA.

Ligations are performed in 15-30 $\mu$l volumes under the following standard conditions and temperatures: 20 mM Tris-Cl pH 7.5, 10 mM MgCl₂, 10 mM DTT, 33 $\mu$g/ml BSA, 10 mM-50 mM NaCl, and either 40 $\mu$M ATP, 0.01-0.02 (Weiss) units T4 DNA ligase at 14° C. (for "sticky end" ligation) or 1 mM ATP, 0.3-0.6 (Weiss) units T4 DNA ligase at 14° C. (for "blunt end" ligation). Intermolecular "sticky ends" ligations are usually performed at 33-100 $\mu$g/ml total DNA concentrations (5-100 nM total end concentration). Intermolecular blunt end ligations (usually employing a 10-30 fold molar excess of linkers) are performed at 1 $\mu$M total ends concentration.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of Na⁺ and Mg⁺² using about 1 unit of BAP per $\mu$g of vector at 60° C. for about one hour. In order to recover the nucleic acid fragments, the preparation is extracted with phenol/chloroform and ethanol precipitated and desalted by application to a Sephadex G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis is used according to the method of Zoller, M. J., et al, *Nucleic Acids Res* (1982) 10:6487-6500. This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered. Details of site specific mutation procedures are described below in specific examples.

C.4. Verification of Construction

Correct ligations for plasmid construction are confirmed by first transforming *E. coli* strain MM294 obtained from *E. coli* Genetic Stock Center, CGSC #6135, or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, *Proc Natl Acad Sci (USA)* (1969) 62:1159, optionally following chloramphenicol amplification (Clewell, D. B., *J Bacteriol* (1972) 110:667). The isolated DNA is analyzed by restriction and/or sequenced by the dideoxy method of Sanger, F., et al, *Proc Natl Acad Sci (USA)* (1977) 74:5463 as further described by Messing, et al, *Nucleic Acids Res* (1981) 9:309, or by the method of Maxam, et al, *Methods in Enzymology* (1980) 65:499.

C.5. Hosts Exemplified

Host strains used in cloning and expression herein are as follows:

For cloning and sequencing, and for expression of construction under control of most bacterial promoters, E. coli strain MM294 (supra), Talmadge, K., et al, Gene (1980) 12:235; Meselson, M., et al, Nature (1968) 217:1110, was used as the host. For expression under control of the $P_LN_{RBS}$ promoter, E. coli strain K12 MC1000 lambda lysogen, $N_7N_{53}cI857SusP_{80}$, ATCC 39531 (hereinafter sometimes referred to as MC1000-39531) is used. To verify the presence of an insert, strains complementing the characteristic of the backbone vector in the region of the insert are used. For example, for the pUC series, E. coli strain DG99, which produces blue colonies on X-gal indicator medium in the absence of insert and white colonies in the presence of insert is used.

D. Examples

The following examples are intended to illustrate, but not to limit, the invention.

D.1. Preparation of a Source for Plasmid Met-Aminopeptidase Encoding DNA

Chromosomal DNA was extracted from E. coli Strain CM89 (supra) by the method of Silhavy, T. J., et al, Experiments with Gene Fusions (1984), Cold Spring Harbor Laboratory, New York, 137–139, and stored in 10 mM Tris, pH 8.0, 1 mM EDTA (TE) buffer. The DNA was digested with Sau3AI at 0.1 U/μg and 0.2 U/μg for 1 hr at 37° C. After reaction termination and ethanol precipitation, the partially digested DNAs were pooled and fractionated on a 10–40% sucrose gradient using a Beckmann SW28 rotor at 26,000 rpm for 24 hr at 15° C. Fractions containing 4–8 kb fragments were pooled, purified on a DE52 column, ethanol precipitated from the eluant, and stored in TE buffer.

A 4 μg portion of the chromosomal DNA was then lighted with 0.5 μg of BamHI-digested, BAP-treated pUC18 vector fragments. The ligation mixture was used to transform E. coli DG99 and plated on lactose indicator plates to confirm the presence of inserts in the plasmids. Approximately 94% of the transformants indeed contained DNA inserts of approximately 4 kb.

Therefore, 18 μl of the ligation mixture was used to transform E. coli MM294 to $Amp^R$ to obtain the gene library. Successful transformants were picked and used to inoculate 700 ml of ampicillin-containing culture medium for plasmid DNA preparation.

Plasmid DNA was obtained from the cells as described in ¶ C.4 (Clewell, D. B., Proc Natl Acad Sci (USA) (1969)) above and used to transform E. coli CM89. Successful transformants selected for $Amp^R$ were plated into microtiter trays for screening and approximately 1,000 colonies were screened.

Single colonies were picked into 200 μl minimal medium (see, for example, U.S. Pat. No. 4,518,584, incorporated herein by reference) supplemented 5% v/v each with 2X L-Broth (DIFCO) plus 1% NaCl, 10% Casamino acids, and 10X yeast nitrogen base. After overnight growth at 37° C, cells were washed twice in 0.1M Tris·HCl pH 7.4. The cells were lysed by adding 20 μl of a 1 mg/ml lysozyme solution in the same buffer, followed by 3 cycles of freeze-thaw. Then 180 μl 0.1M potassium phosphate buffer ($KPO_4$) pH 7.4×0.2 mM $CoCl_2$, containing 72 μg Met-Gly-Met-Met, 36 μg L-amino acid oxidase, 4–5 μg horseradish peroxidase, and 18 μg O-dianisidine dihydrochlorie was added to each well. Of the approximately 1000 colonies screened, 10 showed increased rate of release of Met from Met-Gly-Met-Met, and were further screened for failure to release Leu from Leu-Gly-Gly under the same conditions. One successful colony was designated pSYC1174. E. coli pSYC1174 was deposited with the American Type Culture Collection 27 August 1985 and has accession number 53245.

Plasmid DNA designated pSYC1174 was prepared and sequenced using the dideoxy method as set forth in ¶ C.4 above. The results, along with the deduced amino acid sequence are shown in FIG. 2. The open reading frame encodes a 264 amino acid protein having an N-terminal sequence which corresponds to that of FIG. 1.

D.2. Characteristics of Met-Aminopeptidase from E. coli pSYC1174

The Met-aminopeptidase was purified from crude extracts of E. coli pSYC1174 and the purified protein was analyzed for ability to release amino acids using a variety of peptide substrates.

For purification, overnight cultures of E. coli pSYC1174 in Brian Heat Infusion broth were washed twice in $KPO_4$ buffer (20 mM, pH 7.4) with 0.2 mM $CoCl_2$, and sonicated. PMSF (0.1 mM) was added to the sonicate. The sonicate was centrifuged, and the supernatant passed over DEAE-Sepharose Fast Flow. The enzyme was eluted with a NaCl gradient, 0–0.25M, in the same buffer. Fractions with Met-aminopeptidase activity were pooled, concentrated using 30,000 MW Centricon filters, and passed over an S-200 Sephacryl column, in the same buffer plus 1 mM methionine. Active fractions were pooled and concentrated as before.

The subunit molecular weight was determined to be approximately 32,000 by reducing SDS PAGE (Laemmli, J Mol Biol (1973) 80:575–599), and enzyme purity was estimated to be 95%. The protein is thus of approximately the predicted size for a 264 amino acid protein.

N-terminal sequencing was performed on the purified peptidase. Results for the first 65 amino acids are given in FIG. 1.

Purified Met-aminopeptidase was analyzed for the ability to release amino acids from a variety of peptide substrates, using a modified L-amino acid oxidase-HRP-ODAD assay (described above) and TLC method. The TLC method used silica gel plates with a solvent mixture of n-butanol-acetic acid-water (120:50:30 v/v). Amino acids released were detected and identified after spraying the plates with ninhydrin reagent.

Methionine was released from the following peptides:
Met-Ala-Met;
Met-Gly-Met-Met;
Met-Gly-Met;
Met-Ala-Ser;
Met-Gly-Gly;
Met-Ala-Pro-Thr-Ser-Ser-Ser-Thr-Lys-Lys-Thr-Gln-Leu; and
Met-Pro-Thr-Ser-Ser-Ser-Thr-Lys-Lys-Gln-Leu-Cys.
No amino acids were released from:
Met-Phe-Gly;
Met-Phe-Ala-Gly;
Met-Leu-Phe;
Met-Met-Met;
Leu-Leu-Leu;
Leu-Gly-Gly;

Met-Ala;
Leu-Gly;
Leu-Ala-Pro-Thr-Ser-Ser-Ser-Thr-Lys-Lys-Thr-Gln-Leu;
N-formyl-Met-Met-Met;
Met-Phe;
Met-Ser;
Val-Gly-Gly;
Thr-Gly-Gly;
Trp-Gly-Gly;
Phe-Gly-Gly;
Met-Glu-His-Phe-Arg-Try-Gly;
Met-Lys-Arg-Pro-Pro-Gly-Phe-Ser-Pro-Phe-Arg;
Gly-(Gly)$_3$-Gly;
Phe-Gly-Gly;
Ser-Ser-Ser;
Pro-Thr-Ser-Ser-Ser-Thr-Lys-Lys-Gln-Leu-Cys;
Ala-Pro-Thr-Ser-Ser-Ser-Thr-Lys-Lys-Gln-Leu;
Thr-Val-Leu;
Arg-Gly-Gly;
Ala-(Ala)$_2$-Ala;
Ala-Ala-Ala;
Glu-Gly-Phe;
Leu-Leu-Leu;
Tyr-Gly-Gly;
Ile-Gly-Gly;
Met-Arg-Phe acetate.

The peptidase activity was completely inhibited by 1 mM EDTA and requires about 1–200 mM phosphate ion and 0.02–2.0 mM Co$^{+2}$ for maximum activity.

From the foregoing results, it is clear that the peptidase cleaves only N-terminal methionine and has other specificity requirements as well. The nature of the second and third amino acid in sequence appears to be significant, and a minimum of three amino acids in the peptide appears to be required. The results on short chain peptides may not, however, be completely determinative in terms of the requirements for succeeding amino acids, as folding in larger proteins may provide secondary and tertiary structures which alter the specificity as regards residues 2 and 3. In addition, the specificity is dependent on conditions, and peptides which fail to undergo hydrolysis under the specific conditions used may yet be hydrolyzed if the conditions are altered.

D.3. Preparation of N-Terminal Met-less IL-2

E. coli MM294 carrying pSYC1143, an expression vector for a recombinant IL-2 mutein with the N-terminal sequence in the mature protein: Ala-Pro-Thr-Ser, under the control of the trp promoter was transformed with plasmid DNA (designated pSYC1174) prepared from E. coli pSYC1174. Successful transformants were selected by Amp$^R$ and Tet$^R$, showing the presence of both desired plasmids.

Cells containing both plasmids were grown overnight at 37° C. in minimal medium plus tryptophan 50 mg/l, casamino acids 5 g/l, and both ampicillin 50 mg/l and tetracycline 5 mg/l. The culture was then washed and resuspended in the same medium minus tryptophan, in order to de-repress IL-2 synthesis, and incubated at 37° C. for 4 hr.

The IL-2 thus produced is contained in intracellular refractile bodies. The refractile bodies were purified by repeated sonication and washing in 8 mM EDTA and finally resuspended in 5% SDS. The IL-2 was further purified by HPLC, using a Vydac C4 reverse phase column and a gradient of water to acetonitrile in 0.1% trifluoroacetic acid. The N-terminal sequence was determined for the purified IL-2, and showed the following mixture:

| | |
|---|---|
| Met—Ala—Pro— | 0–5% |
| Ala—Pro— | 25–30% |
| Pro— | 70–75% |

Control cultures grown and induced as above, but containing only pSYC1143 gave produced IL-2 wherein the purified protein has the composition 70% Met-Ala-Pro and 30% Ala-Pro.

(pSYC1143 contains the IL-2 sequences under the control of the trp promoter and the cry positive retroregulator sequence. It is prepared from pFC51.T, which contains this expression system as a 0.95 kb EcoRI fragment, and pACYC184, which is a host vector compatible with pUC18 carrying a Cm$^R$ marker. The expression system is prepared as an EcoRI digest of pFC51.T and ligated into EcoRI-digested pACYC184 to obtain pSYC1143. pFC51.T is extensively described in U.S. Ser. No. 717,331, filed 29 March 1985, assigned to the same assignee and incorporated herein by reference.)

D.4. In Vitro Processing of Met-IL-2

The purified Met-aminopeptidase was also used to process the purified IL-2 in vitro. The reaction mixture contained 50 μl of stock solution containing 1.7 mg/ml of IL-2 prepared as in ¶E.3 above in 0.05% SDS; 40 μl of 0.1M potassium phosphate buffer, pH 7.5 containing 0.2 mM CoCl$_2$; and 10 μl of a 1:10 dilution of purified (¶E.2) Met-aminopeptidase stock containing 8 mg/ml. The reaction mixture was incubated at 30° overnight and the degree of processing assessed using SDS PAGE and N-terminal sequencing. FIG. 3 shows the results of SDS PAGE performed on the unreacted IL-2 and IL-2 in the presence of enzyme. After incubation, the presence of a slightly smaller molecular weight protein replaces the band shown by the original Met-preceded protein. The N-terminal sequence for the purified IL-2 before enzyme treatment was 74% Met-Ala-Pro- and 26% Ala-Pro; after enzyme treatment, it was 94% Ala-Pro- and 6% Met-Ala-Pro.

On 27 August 1985, E. coli strain pSYC1174 was deposited with the American Type Culture Collection (ATCC 53245) under the terms of the Budapest Treaty on the International Recognition of the Deposit of Microorganisms for the Purposes of Patent Procedure and the Regulations thereunder (Budapest Treaty). This assures maintenance of a viable culture for 30 years from data of deposit. The organisms will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention of the rights granted under the authority of any government in accordance with its patent laws.

We claim:

1. A method to obtain a DNA sequence encoding a bacterial Met-aminopeptidase, wherein said Met-aminopeptidase has a specificity whereby it effects cleavage of the N-terminal methionine residue from Met-preceded peptides or proteins without cleavage of internal methionine residues and does not cleave at other N-terminal residues,
   which method comprises:
   preparing a plasmid-borne gene library from a first bacterial strain;
   transforming said gene library into a second bacterial strain that is deficient in general peptidase activity;
   screening transformants for Met-aminopeptidase activity; and
   recovering plasmid DNA from transformants having said activity.

2. The method of claim 1 wherein the first bacterial strain is deficient in peptidase activity.

3. The method of claim 2 wherein the first bacterial strain and second bacterial strain are the same.

4. A method to obtain a DNA sequence encoding a bacterial Met-aminopeptidase, wherein said Met-aminopeptidase has a specificity whereby it effects cleavage of the N-terminal methionine residue from Met-preceded peptides or proteins without cleavage of internal methionine residues and does not cleave at other N-terminal residues,
   which method comprises:
   screening bacterial transformants for Met-aminopeptidase activity, and recovering plasmid DNA from transformants having such activity;
   wherein the transformants were prepared by preparing a plasmid-borne gene library from a first bacterial strain; and
   transforming said gene library into a second bacterial strain that is deficient in general peptidase activity.

5. The method of claim 4 wherein the first bacterial strain is deficient in peptidase activity.

6. The method of claim 5 wherein the first bacterial strain and the second bacterial strain are the same.

7. The method of claim 6 wherein the bacterial strain is *E. coli* CM89.

8. A recombinant bacterium which contains a plasmid functional in expressing DNA encoding Met-aminopeptidase, wherein said Met-aminopeptidase has a specificity whereby it effects cleavage of the N-terminal methionine residue from Met-preceded peptides or proteins without cleavage of internal methionine residues and does not cleave at other N-terminal residues, and
   a vector functional in expressing the DNA encoding a Met-preceded desired recombinant foreign protein,
   wherein the Met-aminopeptidase has a specificity wherein methionine is released from a peptide selected from the group consisting of:
   Met-Ala-Met;
   Met-Gly-Met-Met;
   Met-Gly-Met;
   Met-Ala-Ser;
   Met-Gly-Gly;
   Met-Ala-Pro-Thr-Ser-Ser-Ser-Thr-Lys-Lys-Thr-Gln-Leu;
   Met-Pro-Thr-Ser-Ser-Ser-Thr-Lys-Lys-Gln-Leu-Cys;
   and no amino acids are released from a peptide selected from the group consisting of:
   Met-Phe-Gly;
   Met-Phe-Ala-Gly;
   Met-Leu-Phe;
   Met-Met-Met;
   Leu-Leu-Leu;
   Leu-Gly-Gly;
   Met-Ala;
   Leu-Gly;
   Leu-Ala-Pro-Thr-Ser-Ser-Ser-Thr-Lys-Lys-Thr-Gln-Leu;
   N-formyl-Met-Met-Met;
   Met-Phe;
   Met-Ser;
   Val-Gly-Gly;
   Thr-Gly-Gly;
   Trp-Gly-Gly;
   Phe-Gly-Gly;
   Met-Glu-His-Phe-Arg-Tyr-Gly;
   Met-Lys-Arg-Pro-Pro-Gly-Phe-Ser-Pro-Phe-Arg;
   Gly-(Gly)$_3$-Gly;
   Ser-Ser-Ser;
   Pro-Thr-Ser-Ser-Ser-Thr-Lys-Lys-Gln-Leu-Cys;
   Ala-Pro-Thr-Ser-Ser-Ser-Thr-Lys-Lys-Gln-Leu;
   Thr-Val-Leu;
   Arg-Gly-Gly;
   Ala-(Ala)$_2$-Ala;
   Ala-Ala-Ala;
   Glu-Gly-Phe;
   Leu-Leu-Leu;
   Tyr-Gly-Gly;
   Ile-Gly-Gly; and
   Met-Arg-Phe acetate.

9. The method of claim 1 wherein the Met-aminopeptidase has a specificity wherein methionine is released from a peptide selected from the group consisting of:
   Met-Ala-Met;
   Met-Gly-Met-Met;
   Met-Gly-Met;
   Met-Ala-Ser;
   Met-Gly-Gly;
   Met-Ala-Pro-Thr-Ser-Ser-Ser-Thr-Lys-Lys-Thr-Gln-Leu; and
   Met-Pro-Thr-Ser-Ser-Ser-Thr-Lys-Lys-Gln-Leu-Cys;
and no amino acids are released from a peptide selected from the group consisting of:
   Met-Phe-Gly;
   Met-Phe-Ala-Gly;
   Met-Leu-Phe;
   Met-Met-Met;
   Leu-Leu-Leu;
   Leu-Gly-Gly;
   Met-Ala;
   Leu-Gly;
   Leu-Ala-Pro-Thr-Ser-Ser-Ser-Thr-Lys-Lys-Thr-Gln-Leu;
   N-formyl-Met-Met-Met;
   Met-Phe;
   Met-Ser;
   Val-Gly-Gly;
   Thr-Gly-Gly;
   Trp-Gly-Gly;
   Phe-Gly-Gly;
   Met-Glu-His-Phe-Arg-Tyr-Gly;
   Met-Lys-Arg-Pro-Pro-Gly-Phe-Ser-Pro-Phe-Arg;
   Gly-(Gly)$_3$-Gly;
   Ser-Ser-Ser;
   Pro-Thr-Ser-Ser-Ser-Thr-Lys-Lys-Gln-Leu-Cys;
   Ala-Pro-Thr-Ser-Ser-Ser-Thr-Lys-Lys-Gln-Leu;
   Thr-Val-Leu;
   Arg-Gly-Gly;
   Ala-(Ala)$_2$-Ala;
   Ala-Ala-Ala;
   Glu-Gly-Phe;
   Leu-Leu-Leu;

Tyr-Gly-Gly;
Ile-Gly-Gly; and
Met-Arg-Phe acetate.

10. The method of claim 4 wherein the Met-aminopeptidase has a specificity wherein methionine is released from a peptide selected from the group consisting of:
Met-Ala-Met;
Met-Gly-Met-Met;
Met-Gly-Met;
Met-Ala-Ser;
Met-Gly-Gly;
Met-Ala-Pro-Thr-Ser-Ser-Ser-Thr-Lys-Lys-Thr-Gln-Leu; and
Met-Pro-Thr-Ser-Ser-Ser-Thr-Lys-Lys-Gln-Leu-Cys;
and no amino acids are released from a peptide selected from the group consisting of:
Met-Phe-Gly;
Met-Phe-Ala-Gly;
Met-Leu-Phe;
Met-Met-Met;
Leu-Leu-Leu;
Leu-Gly-Gly;
Met-Ala;
Leu-Gly;
Leu-Ala-Pro-Thr-Ser-Ser-Ser-Thr-Lys-Lys-Thr-Gln-Leu;
N-formyl-Met-Met-Met;
Met-Phe;
Met-Ser;
Val-Gly-Gly;
Thr-Gly-Gly;
Trp-Gly-Gly;
Phe-Gly-Gly;
Met-Glu-His-Phe-Arg-Tyr-Gly;
Met-Lys-Arg-Pro-Pro-Gly-Phe-Ser-Pro-Phe-Arg;
Gly-(Gly)$_3$-Gly;
Ser-Ser-Ser;
Pro-Thr-Ser-Ser-Ser-Thr-Lys-Lys-Gln-Leu-Cys;
Ala-Pro-Thr-Ser-Ser-Ser-Thr-Lys-Lys-Gln-Leu;
Thr-Val-Leu;
Arg-Gly-Gly;
Ala-(Ala)$_2$-Ala;
Ala-Ala-Ala;
Glu-Gly-Phe;
Leu-Leu-Leu;
Tyr-Gly-Gly;
Ile-Gly-Gly; and
Met-Arg-Phe acetate.

11. A method for producing an N-terminal Met-less recombinant protein in a bacterial host which method comprises
culturing a recombinant bacterium which contains a plasmid functional in expressing DNA encoding Met-aminopeptidase, wherein said Met-aminopeptidase has a specificity whereby it effects cleavage of the N-terminal methionine residue from Met-preceded peptides or proteins without cleavage of internal methionine residues and does not cleave at other N-terminal residues, and
a vector functional in expressing the DNA encoding a Met-preceded desired recombinant foreign protein, under conditions appropriate for the expression of said DNAs encoding said Met-aminopeptidase and said desired recombinant foreign protein,
wherein the Met-aminopeptidase has a specificity wherein methionine is released from a peptide selected from the group consisting of:
Met-Ala-Met;
Met-Gly-Met-Met;
Met-Gly-Met;
Met-Ala-Ser;
Met-Gly-Gly;
Met-Ala-Pro-Thr-Ser-Ser-Ser-Thr-Lys-Lys-Thr-Gln-Leu; and
Met-Pro-Thr-Ser-Ser-Ser-Thr-Lys-Lys-Gln-Leu-Cys;
and no amino acids are released from a peptide selected from the group consisting of:
Met-Phe-Gly;
Met-Phe-Ala-Gly;
Met-Leu-Phe;
Met-Met-Met;
Leu-Leu-Leu;
Leu-Gly-Gly;
Met-Ala;
Leu-Gly;
Leu-Ala-Pro-Thr-Ser-Ser-Ser-Thr-Lys-Lys-Thr-Gln-Leu;
N-formyl-Met-Met-Met;
Met-Phe;
Met-Ser;
Val-Gly-Gly;
Thr-Gly-Gly;
Trp-Gly-Gly;
Phe-Gly-Gly;
Met-Glu-His-Phe-Arg-Tyr-Gly;
Met-Lys-Arg-Pro-Pro-Gly-Phe-Ser-Pro-Phe-Arg;
Gly-(Gly)$_3$-Gly;
Ser-Ser-Ser;
Pro-Thr-Ser-Ser-Ser-Thr-Lys-Gln-Leu-Cys;
Ala-Pro-Thr-Ser-Ser-Ser-Thr-Lys-Lys-Gln-Leu;
Thr-Val-Leu;
Arg-Gly-Gly;
Ala-(Ala)$_2$-Ala;
Ala-Ala-Ala;
Glu-Gly-Phe;
Leu-Leu-Leu;
Tyr-Gly-Gly;
Ile-Gly-Gly; and
Met-Arg-Phe acetate.

* * * * *